US 8,759,549 B2

(12) United States Patent
Lee et al.

(10) Patent No.: US 8,759,549 B2
(45) Date of Patent: Jun. 24, 2014

(54) **COMPOUND EXTRACTED FROM *ANTRODIA CINNAMOMEA* AND PHARMACEUTICAL COMPOSITION COMPRISING THE SAME**

(75) Inventors: Ching-Kuo Lee, New Taipei (TW); Pi-Yu Chen, Taipei (TW); Jir-Mehng Lo, Hsinchu County (TW); Wen-Bin Zhong, New Taipei (TW); Tien-Wang Chiu, Taoyuan (TW); Chieh-Chou Yu, Miaoli County (TW)

(73) Assignee: Chieh-Chou Yu, Miaoli County (TW)

( * ) Notice: Subject to any disclaimer, the term of this patent is extended or adjusted under 35 U.S.C. 154(b) by 340 days.

(21) Appl. No.: 13/102,068

(22) Filed: May 6, 2011

(65) Prior Publication Data

US 2012/0029069 A1 Feb. 2, 2012

(30) Foreign Application Priority Data

Jul. 30, 2010 (TW) ................ 99125645 A (51) Int. Cl.
*C07D 317/44* (2006.01)
*A61K 31/36* (2006.01)
(52) U.S. Cl.
USPC .......................... 549/437; 514/464
(58) Field of Classification Search
None
See application file for complete search history.

(56) References Cited

FOREIGN PATENT DOCUMENTS

CN 101214238 A 7/2008

OTHER PUBLICATIONS

*Antrodia cinnamomea* (2009).*
Chia-Lin Lee et al., "First total synthesis of antrocamphin A and its analogs as anti-inflammatory and anti-platelet aggregation agents." Org. Biomol. Chem,. 2011, 9, 70-73.
Anh-Tho Nguyen et al., "A sugar ester and an iridoid glycoside from *Scrophularia ningpoensis*." Phytochemistry. 2005, 66(10): 1186-1191.
NJ Loftus et al., "Global metabolite profiling of human colorectal cancer xenografts in mice using HPLC-MS/MS", J Proteome Res. Jun. 7, 2013;12(6):2980-6. (abstract only).
Yi-Heng Li, et al, "A novel Inhibitory Effect of *Antrodia camphorata* Extract on Vascular Smooth Muscle Cell Migration and Neointima Formation in Mice." Int Heart J Mar. 2009; 50(2):207-20.
Chinese Office Action for China application No. 201110296973.0, dated Jan. 23, 2014.

* cited by examiner

*Primary Examiner* — Andrew D Kosar
*Assistant Examiner* — Raymond Covington
(74) *Attorney, Agent, or Firm* — Lowe Hauptman & Ham, LLP (57) ABSTRACT

This invention relates to a novel compound extracted from *antrodia Cinnamomea* and related compounds of formula (1), and pharmaceutical compositions comprising the compound of formula (1) and a pharmaceutically acceptable carrier or excipient. The invention further comprises the method of inhibit cancer cells by administering an effective amount of the compound of formula (1).

Formula (1)

12 Claims, 7 Drawing Sheets

COMPOUND EXTRACTED FROM *ANTRODIA CINNAMOMEA* AND PHARMACEUTICAL COMPOSITION COMPRISING THE SAME

FIELD OF INVENTION

The present invention relates to novel compound extracted from *antrodia Cinnamomea* and related compounds of formula (1), pharmaceutical compositions comprising the compounds of formula (1), and methods of their use in inhibiting cancer cells.

BACKGROUND OF THE INVENTION

*Antrodia Cinnamomea*, a native Taiwan fungus, is also known as *antrodia* camphorate, Niu-chang mushroom, Chang chih, Hong-chang, Hong-chang mushroom, or Chang-nei mushroom. Its spores grow on the inner cavity of the decayed cinnamomum Kanehirai Hey, at an altitude between 450 to 2,000 meters. It is a perennial mushroom belonging to the *Antrodia* genus and the Polyporaceae family. The wild cinnamomum Kanehirai Hey is a rare and protected plant species in Taiwan. Due to the rampant illegal logging in recent years, there is much less cinnamomum Kanehirai Hey in the wilderness. In addition, *antrodia Cinnamomea* has a relatively shortened growth period, from June to October of each year. Thus, *antrodia Cinnamomea* is a precious and expensive herbal medicine.

*Antrodia Cinnamomea* comprises many complex ingredients, including polysaccharides (for example, β-dextran), triterpenoids, superoxide dismutase, adenosine, proteins (including immunoglobulin), vitamins (for example, vitamin B and nicotinic acid), trace elements (for example, calcium, phosphorus, and germanium), nucleic acid, agglutinin, amino acids, steroids, lignin, and blood pressure stabilizing substances (for example, antodia acid). These physiologically active substances have been shown to suppress tumors, enhance immunity, mediate allergic response, inhibit platelet aggregation, decrease blood glucose, reduce serum cholesterol, and protect the liver.

Although *antrodia Cinnamomea* contains many physiologically active substances, not all of them have been identified. It will be desirable to identify, purify and analyze an *antrodia Cinnamomea* extract to obtain an active ingredient with anti-tumor activity, as a safe and effective alternative for treating or preventing cancer.

SUMMARY OF THE INVENTION

The present invention is directed to compounds of formula (1) and to pharmaceutical compositions comprising the compound of formula (1), which can achieve the effect of cancer cell inhibition.

The present invention relates to a novel compound, which has the formula (1),

Formula (1)

a prodrug thereof or a pharmaceutically acceptable salt of said compound or said prodrug, wherein $R_1$, $R_2$, and $R_3$ are, independently, hydrogen, alkoxy, hydroxyl, carboxyl, or alkyl.

The present invention further provides a method for extracting compound of formula (1) from *antrodia Cinnamomea*, and a pharmaceutical composition comprising the compound of Formula (1) or a prodrug thereof, and a pharmaceutically acceptable excipient or carrier.

Based on the above, the compound extracted from *antrodia* camphorate of the present invention and the pharmaceutical composition containing the same may have one or more of the following advantages.

(1) The compound of the present invention is a novel compound extracted from *antrodia camphorate*, and has an activity of inhibiting human colorectal cancer cells, thus bring a new opportunity for preventing and treating of colorectal cancer.

(2) A pharmaceutical composition, preferably as a tablet or a powder, may be formulated by adding the compound of the present invention which has an activity of inhibiting growth of tumor cells into other compatible salts or a pharmaceutically acceptable excipient or carrier, for being orally taken by a patient, so as to increase the inhibition effect of the tumor cells in the patient.

DETAILED DESCRIPTION OF THE INVENTION

Definitions

When present, unless otherwise specified, the following terms are generally defined as, but are not limited to, the following:

"Alkyl" refers to groups of from 1 to 5 carbon atoms inclusively, either straight chained or branched, or saturated or unsaturated hydrocarbon chains.

"Alkoxy" refers to the group alkyl-O— wherein the alkyl group is as defined above including optionally substituted alkyl groups as also defined above.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

The term "treating," "treated," or "treatment" as used herein includes preventative (e.g. prophylactic), palliative, and curative uses or results.

The term "subject" refers to animal, including mammals, preferably humans.

The term "prodrug" means a compound of formula (1) or a pharmaceutically acceptable salt of the compound of formula (I) that is transformed in vivo to yield a biologically active product. The transformation may occur by various mechanisms, such as through hydrolysis in blood, or biotransformation (e.g., enzymatic activity). A prodrug of a compound of formula (1) may be formed in a convention manner, for example, by modifying functional group present in the compound, such as a hydroxyl group and yield a free hydroxyl.

A "pharmaceutically acceptable carrier" or "pharmaceutically acceptable excipient" refers to a carrier or excipient that, after administration to or upon a subject, does not cause undesirable physiological effects. The carrier in a pharmaceutical composition must be "acceptable" also in the sense that is compatible with the active ingredient and, preferably, capable of stabilizing it. One or more solubilizing agents can be utilized as pharmaceutical carriers for delivery of a compound of formula (1).

Novel Compound

The present invention is directed to a compound of formula (I),

Formula (1)

a prodrug thereof or a pharmaceutically acceptable salt of said compound or said prodrug, wherein $R_1$, $R_2$, and $R_3$ are each independently hydrogen, alkoxy, hydroxyl, carboxyl, or alkyl.

In accordance with this invention, compounds of Formula (1) can be synthetically produced by the following reaction scheme.

synthetic route

REFERENCE

Org. Biomol. Chem., 2011, 9, 70-73, by C. L. Lee et al.

In a preferred embodiment, the compound of the present invention has the structure of formula (2)

Formula (2)

The compound of formula (1) is extracted from *antrodia Cinnamomea* using water or an organic solvent. The organic solvent may be an alcohol, an ester, an alkane, or a haloalkane.

The alcohol solvent as used in the invention comprises of methanol, ethanol, or propanol. The ester solvent as used in the invention comprises of ethyl acetate. The alkane solvent as used in the invention comprises of hexane. The haloalkane solvent as used in the invention comprises of chloromethane or chloroethane. The compound of the present invention is preferably extracted using an alcohol solvent.

The Pharmaceutical Composition

The pharmaceutical composition comprises the compound of formula (I) and a pharmaceutically acceptable carrier or excipient. Suitable pharmaceutically acceptable carriers are well known in the art and vary with the desired form and mode of administration of the pharmaceutical composition. The pharmaceutically acceptable carrier or excipient include, but are not limited to, saline solution, aqueous electrolyte solutions, isotonicity modifiers, water, polyethers such as polyethylene glycol, polyvinyls such as polyvinyl alcohol and povidone, cellulose derivatives such as methylcellulose and hydroxypropyl methyl cellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical composition can be prepared for inhalation, topical, oral, rectal, implanted reservoir and parenteral (such as intravenous, intramuscular, subcutaneous, intra-articular, intra-synovial, cisternal, intrathecal, intrahepatic, intralesional and intracranial) delivery. Oral administration is preferred.

The pharmaceutical composition can be prepared by any method known in the art of pharmacy. Such methods include the step of brining into association the active compound with the carrier which may encompass one or more accessory ingredients. For instance, to prepare compositions suitable for injection, solutions and suspensions are sterilized and are preferably isotonic to blood. In making injectable preparations, carriers which are commonly used in this field are used, for example, water, ethyl alcohol, propylene glycol. In these instances, adequate amounts of isotonicity adjusters such as sodium chloride, glucose or glycerin can be added to make the preparations isotonic. The aqueous sterile injection solution may further comprise oxidants, buffers, and the like additions acceptable for parenteral composition.

For instance, the oral administration can be in the form of a tablet, hard or soft capsule lozenges, aqueous or oily suspensions, viscous gels, chewable gums, dispersible powders or granules, emulsion, or syrups or elixirs.

Powders are prepared by comminuting the compound to a suitable fine size and mixing with a similarly comminuted pharmaceutical carrier such as an edible carbohydrate, as, for example, starch or mannitol. Flavoring, dispersing and coloring agents can also be present.

For oral use, an aqueous suspension is prepared by addition of water to dispersible powders and granules with a dispersing or wetting agent, suspending agent, one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anhydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active compound is mixed with an inert solid diluent, for example, calcium carbonate, calcium phosphate or kaolin, or as soft gelatin capsules wherein the active compound is mixed with water or an oil medium, for example, peanut oil, liquid paraffin or olive oil. Formulation for oral use can also be presented as chewable gums by embedding the active compound in gums so that the active compound is slowly released upon chewing.

The Method of Inhibiting Cancer Cells

The method according to the present invention comprises the administration of an effective amount of compound of formula (1) to the subject, whereby the symptoms and signs of the cancer in the subject are reduced. These active compounds include the compounds of formula (1), a prodrug thereof, or a pharmaceutically acceptable salt of said compound or prodrug.

An "effective amount," as used herein, refers to a dose of the compound of formula (1) that is sufficient to reduce the symptoms and signs of cancer, such as mass, pain, and weight loss.

Throughout the specification and claims, a given chemical formula name shall encompass all optical and stereoisomers, as well as racemic mixtures where such isomers and mixtures exist.

The following examples further illustrate the present invention. These examples are intended merely to be illustrative of the present invention and are not to be construed as being limiting.

EXAMPLES

Example 1

Extraction and Identification of Compound of Formula (2)

The compound of formula (2) was extracted from *antrodia Cinnamomea* cultivated on satinwood, as illustrated below:
1. The *antrodia Cinnamomea* is grinded into powder and mixed with ethanol, to obtain an ethanol extract of *antrodia Cinnamomea*;
2. The ethanol extract in Step 1 was dispersed in a mixture of ethyl acetate and water (volume ratio 1:1) to start the partition process;
3. The high polar ethanol extract was dissolved in water to form an aqueous solution (the lower layer) and the low polar ethanol extract was dissolved in ethyl acetate (the upper layer).

The ethyl acetate solution in Step 3 was fractionated into seven portions and analyzed by column chromatography. These seven portions were further isolated through column chromatography and purified through HPLC. A compound having aromatic properties was identified.

The chemical structure of the compound of formula (2) was identified by the following steps:
1. The (M+H)$^+$ molecular weight of the isolated compound was 261.1038. This was calculated by the high-resolution electron spray ionization mass spectrometer (HRESIMS) in a positive-ion mode. The molecular formula of the isolated compound was $C_{15}H_{16}O_4$, and the unsaturation degree was 8.
2. The structure of the isolate compound was assessed by the following methods: $^1$H-NMR and $^{13}$C NMR were performed using a 500 MHz NMR spectrometer, COSY, HMQC and HMBC NMR spectrum. The deuterium solvent was $CDCl_3$.

Figure 1:
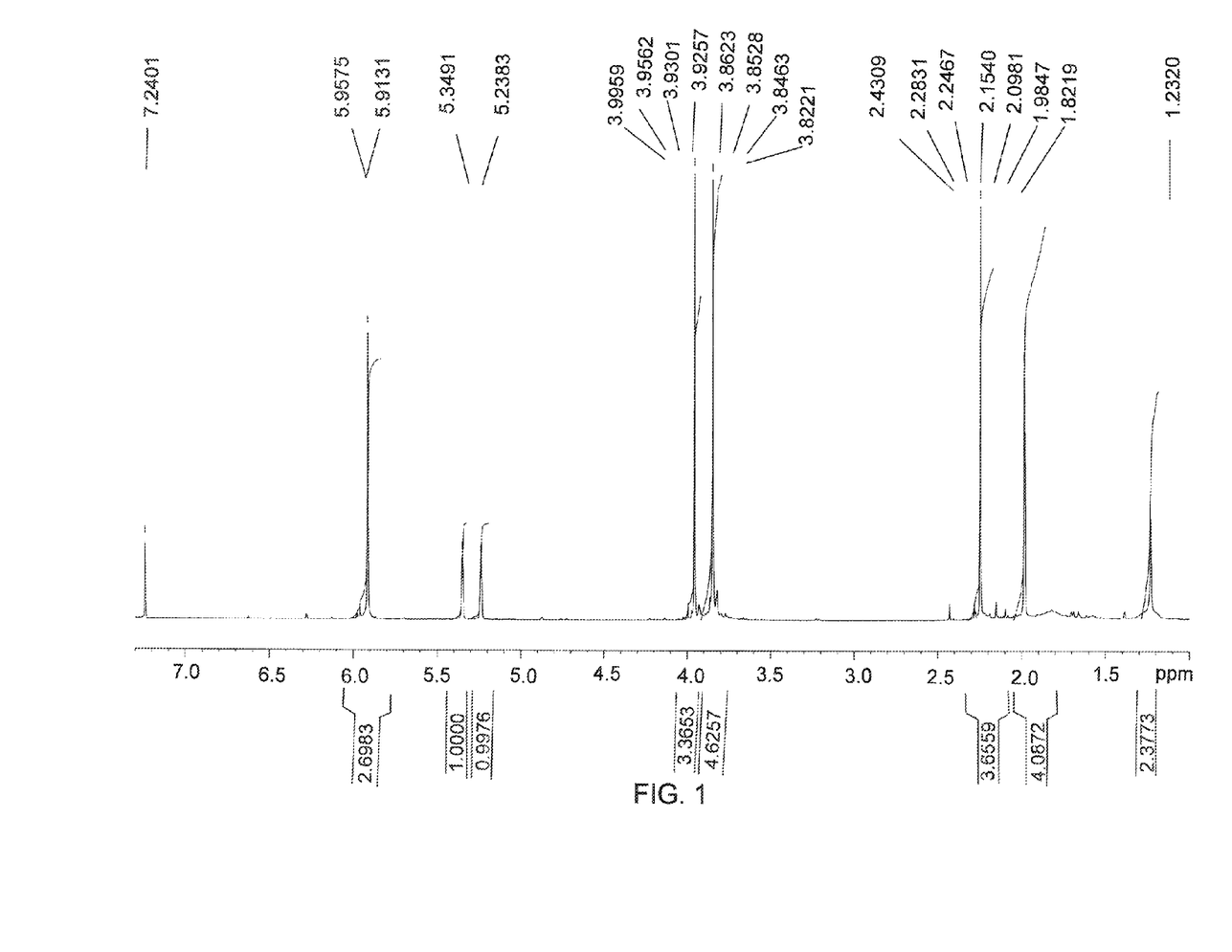
FIG. 1 shows the one-dimensional proton nuclear magnetic resonance ($^1$H-NMR) spectrum of the compound of formula (I).

FIG. 1 shows the one-dimensional $^1$H-NMR spectrum of the isolated compound.

$^1$H-NMR (500 MHz, $CDCl_3$): $\delta_H$ 5.91 (2H, s), 5.35 (1H, br s), 5.24 (1H, br s), 3.96 (3H, s), 3.85 (3H, s), 2.25 (3H, s), 1.98 (3H, br s). The NMR spectrum also showed proton signals of a methylene having two oxygen atoms attached thereon, two protons on a double bond alkene, two methoxy groups, one methyl attached to a phenyl ring, and one proton in methyl attached to an alkene.

Figure 2:
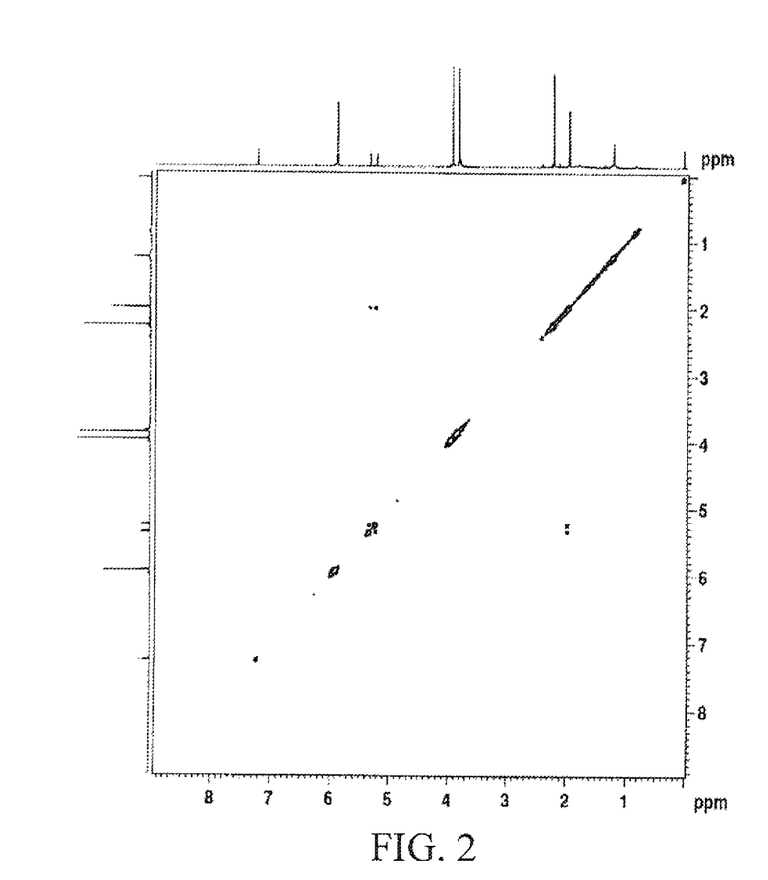
FIG. 2 shows the correlation spectroscopy (COSY) two-dimensional NMR spectrum of the compound of formula (I).

FIG. 2 shows a two-dimensional COSY NMR spectrum of the isolated compound. According to FIG. 2, $\delta_H$ 1.98 correlates with $\delta_H$ 5.35, 5.24. This confirms that methyl at $\delta_H$ 1.98 is linked to an alkene.

Figure 3:
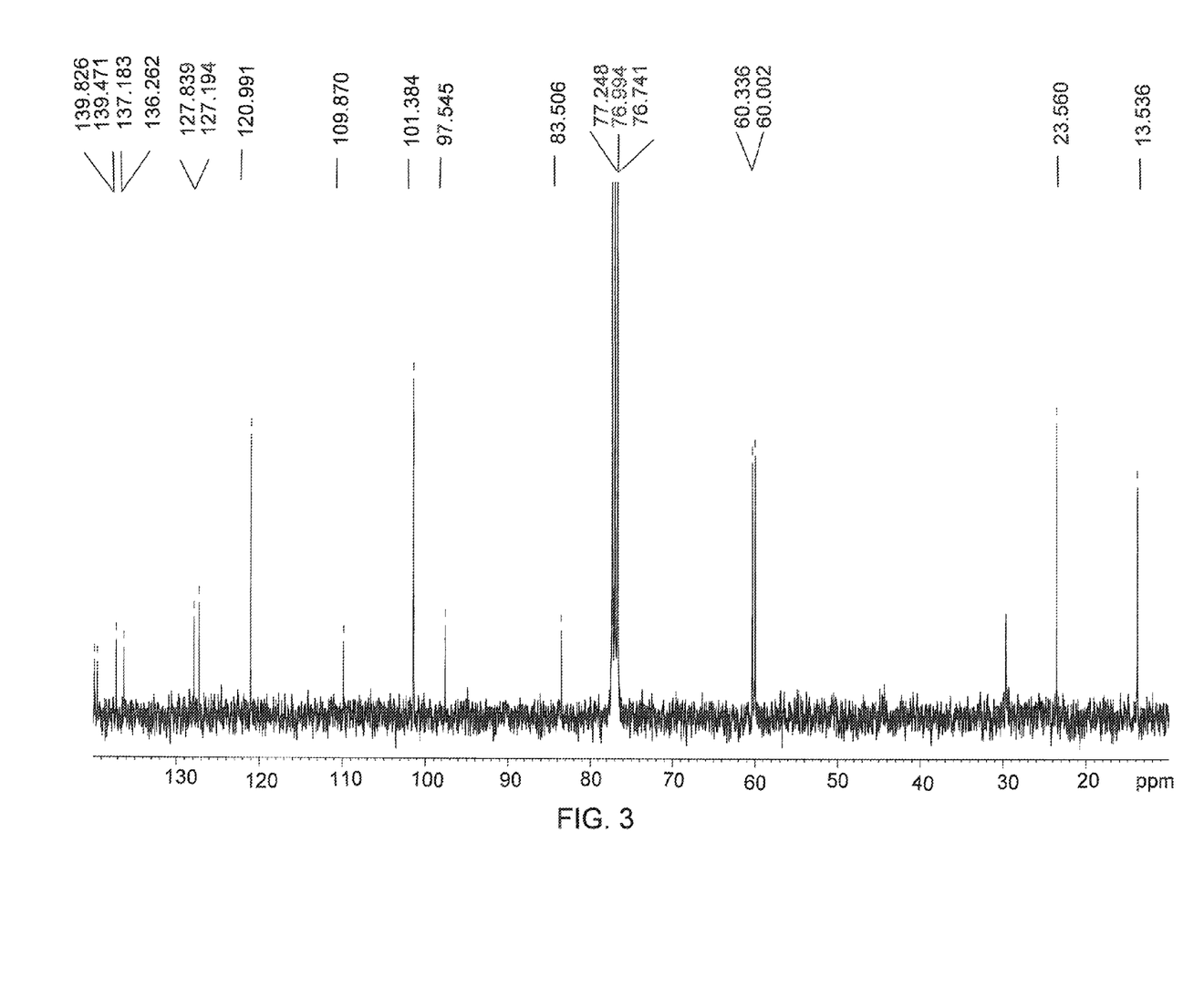
FIG. 3 shows the one-dimensional $^{13}$C NMR spectrum of the compound of formula (I).

FIG. 3 shows a one-dimensional $^{13}$C NMR spectrum of the isolated compound, wherein an aromatic ring has the chemical shift at $\delta_C$ 139.8, 139.5, 137.2, 136.3, 127.8, 101.4, the carbon signals of the four methyl groups are at $\delta_C$ 60.3, 60.0, 13.8, 23.6, and a methylene group attached with 2 oxygen atoms is located at $\delta_C$ 101.4. The two characteristic carbon signals for alkynes are at $\delta_C$ 97.5 and 83.5. Based on the HRESIMS analysis, the unsaturation degrees of the isolated compound are as follows: the aromatic ring has 4 degrees of unsaturation, the two double-bond alkenes have 1 degree of unsaturation each, and the remaining two degrees of unsaturation were identified in an alkyne moiety.

Figure 4:
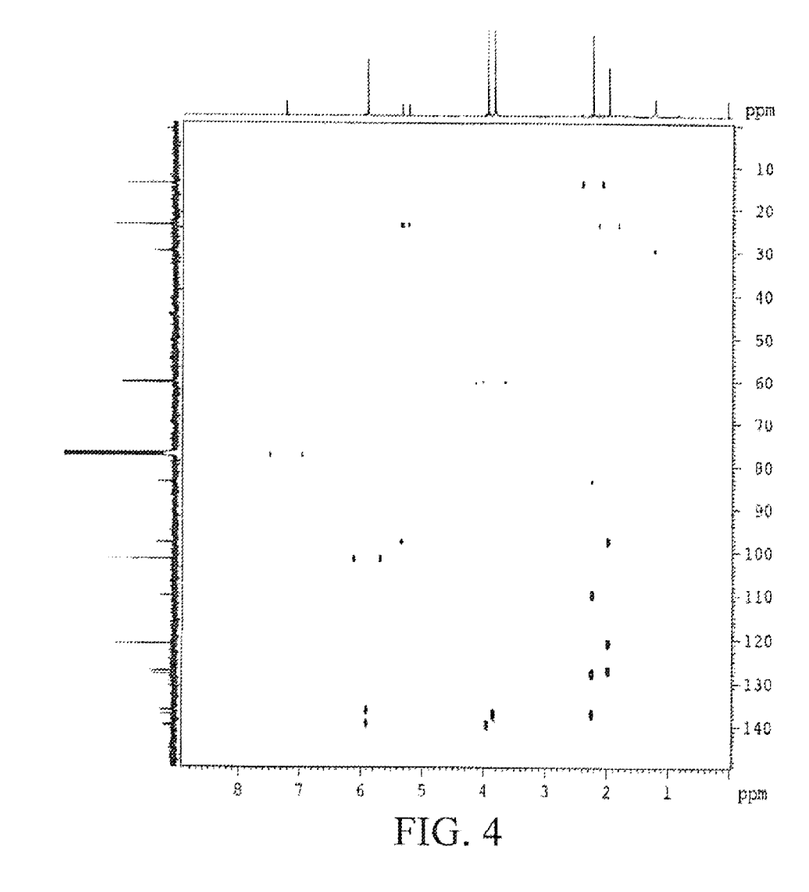
FIG. 4 shows the two-dimensional Heteronuclear Multiple Quantum Coherence (HMQC) NMR spectrum of the compound of formula (I).

FIG. 4 shows the HMQC NMR spectrum of the isolated compound. The carbon chemical shifts ($\delta_C$) correlates with the proton chemical shifts are located at the following 6 positions: 101.4, 121.0, 60.3, 60.0, 13.8, and 23.6.

Figure 5:
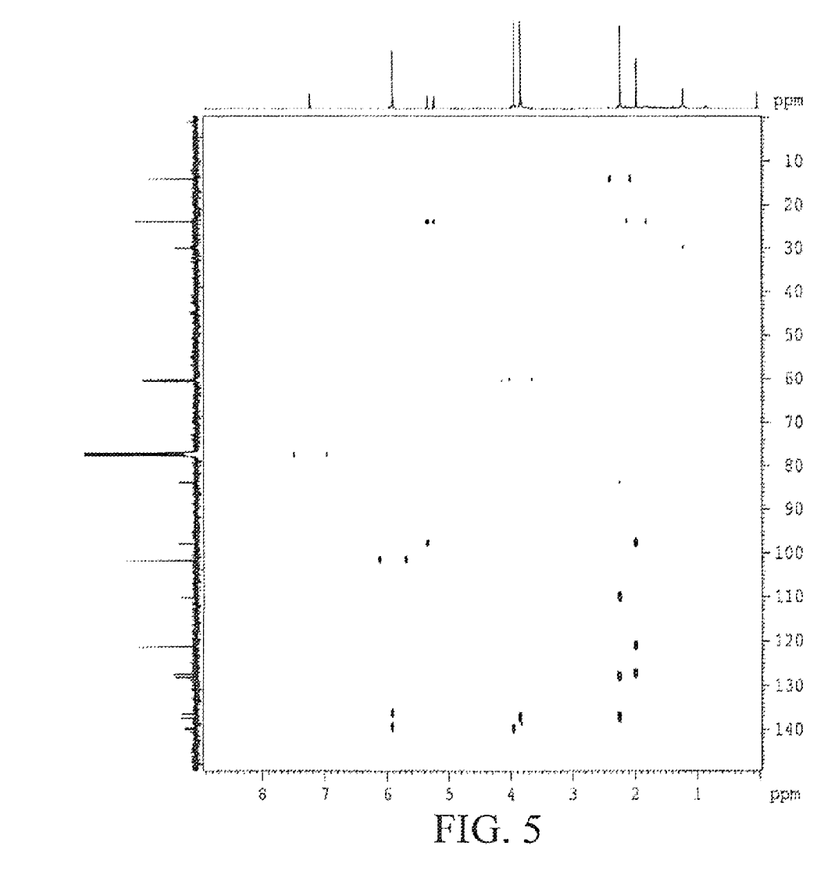
FIG. 5 shows the two-dimensional Heteronuclear Multiple Bond Coherence (HMBC) NMR spectrum of the compound of formula (I).

FIG. 5 shows the HMBC NMR spectrum of the isolated compound. The isolated compound has a long distance coupling at $\delta_H$ 1.98 with a carbon chemical shift at $\delta_C$ 97.5 (an alkyne). According to the experimental results summarized in Table 1, the isolated compound has the structure of 1,2-methylenedioxy-3,6-bismethoxy-4-(3-methyl-3-alkene-1-butyne)-5-methylbenzene, that is, the compound of formula (2).

TABLE 1

| | | $^1$H-$^1$H COSY | | |
|---|---|---|---|---|
| 1H ($\delta_H$) | | ($\delta_H$) | HMQC ($\delta_C$) | HMBC ($\delta_C$) |
| 1.98 | 1H, br s | 5.24 | 23.6 | 121.0, 127.2, 97.5 |
| | | 5.35 | | |
| 2.25 | 3H, s | | 13.8 | 101.4, 127.8, 137.2 |
| 3.85 | 3H, s | | 60.0 | 137.2 |
| 3.96 | 3H, s | | 60.3 | 139.8 |
| 5.24 | br s | | 121.0 | 127.2, 23.6, 97.5 |
| 5.35 | | | | |
| 5.91 | 2H | | 101.4 | 136.3, 139.5 |

Example 2

In Vitro Anti-Cancer Activity

Relevance:

This test demonstrates the ability of the compound of formula (2) to inhibit human cancer cells in vitro.

Protocol

The anti-cancer effect compound of formula (2) and compounds (3) and (4) were evaluated using the HT29 and Colo205 human colorectal cancer cell lines.

Compounds (3) and (4) are known compounds extracted from *antrodia Cinnamomea* and have the formulas shown below:

Compound (3)

Compound (4)

Human colorectal cancer cells HT29 and Colo205 were plated in a 96-well plate, at a concentration of 1×10$^{4-5}$ cells/well. The human colorectal cancer cells were incubated at 37° C. with 5% $CO_2$ overnight. These cancer cells were washed three times with a serum free medium or a phosphate buffer solution (PBS) the next day. The compound of Formula (2) and Compounds (3) and (4) were added to the HT29 and Colo205 human colorectal cancer cells respectively. The experiment was performed three times and the average $IC_{50}$ value was calculated.

Results

Figure 6:
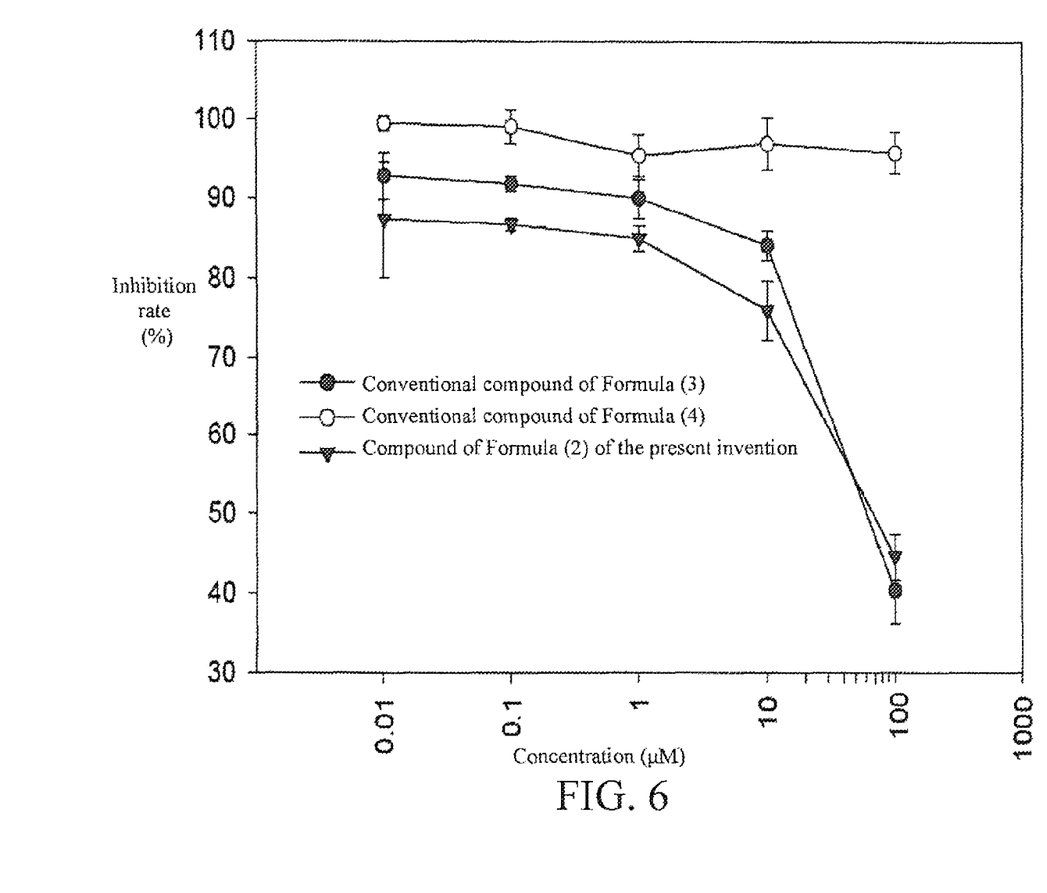
FIG. 6 shows the half-maximal inhibitory concentrations ($IC_{50}$) curves of the compound of Formula (2), Compounds (3) and (4), which measure the effectiveness of the compound in inhibiting human colorectal cancer cells (HT29).
Figure 7:
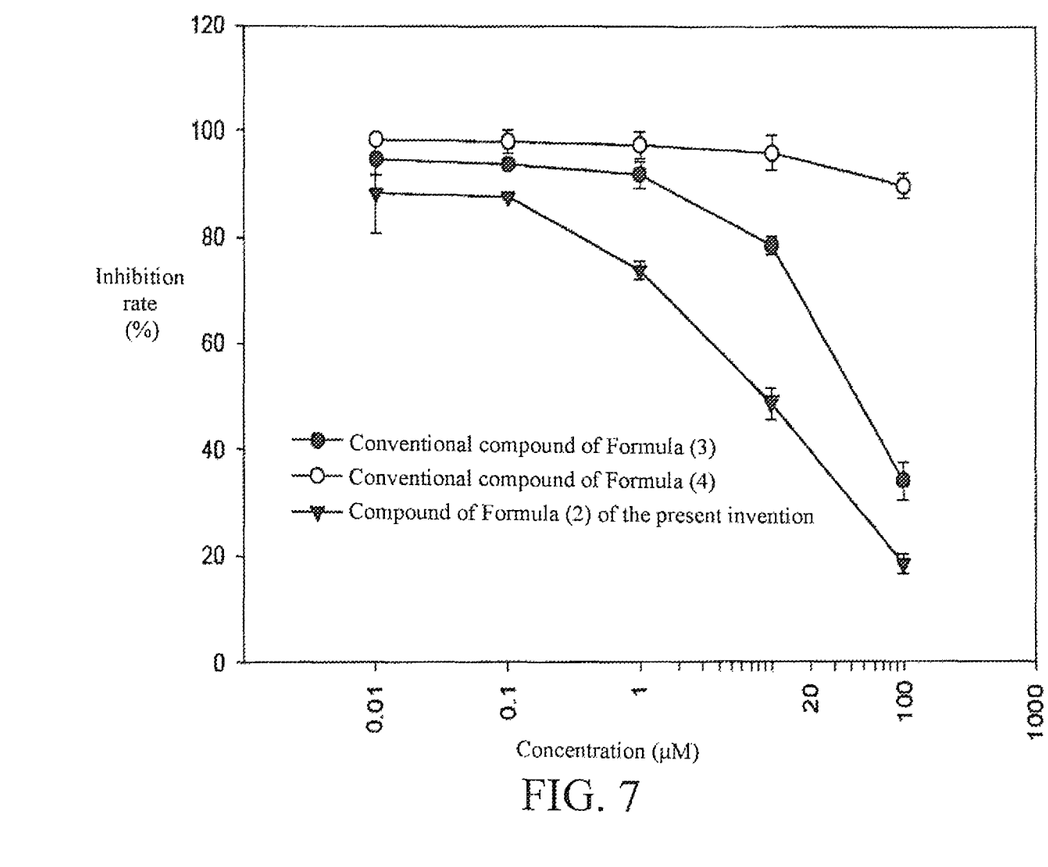
FIG. 7 shows the $IC_{50}$ curves of the compound of Formula (2), Compounds (3) and (4), which measure the effectiveness of the compound in inhibiting human colorectal cancer cells (Colo205).

FIG. 6 shows the $IC_{50}$ curves of the compound of Formula (2) and Compounds (3) and (4) for HT29 human colorectal cancer cells. FIG. 7 shows the $IC_{50}$ curves of the compound of Formula (2) and compounds (3) and (4) for Colo205 human colorectal cancer cells. It has been reported that chemicals with $IC_{50}$ less than 100 M exhibits cytotoxicity. (*Phytochemistry* 2005, 66(10), 1186-1191).

Referring to FIG. 6, the $IC_{50}$ of compound of formula (2) is 66 μM, of compound (3) is 59 μM, and of Compound (4) is higher than 100 μM. This shows the compound of Formula (2) has an enhanced anticancer activity against the tested HT29 human colorectal cancer cell line compared to Compound (4).

Referring to FIG. 7, the $IC_{50}$ of compound of formula (2) is 9 μM, of compound (3) is 42 μM, and of Compound (4) is higher than 100 μM. This shows the compound of Formula (2) has an enhanced anticancer activity against the tested Colo205 human colorectal cancer cell line compared to Compounds (3) and (4). In summary, the compound of formula (2) has a lower $IC_{50}$, and is more effective in inhibiting colorectal cancer cells than known compounds.

Based on the above, the compound of formula (Id) is a novel compound extracted from *antrodia Cinnamomea* and is effective in treating cancer.

We claim:
1. A compound of formula (I)

Formula (I)

or a pharmaceutically acceptable salt thereof,
wherein $R_1$, $R_2$, and $R_3$ are, independently, hydrogen, alkoxy, hydroxyl, carboxyl, or alkyl, provided that $R_1$ and $R_2$ are not methoxy when $R_3$ is methyl.

2. An isolated and purified compound of formula (I)

Formula (I)

or a pharmaceutically acceptable salt thereof,
wherein $R_1$, $R_2$, and $R_3$ are, independently, hydrogen, alkoxy, hydroxyl, carboxyl, or alkyl.

3. The compound of claim 2, wherein $R_1$ and $R_2$ are methoxy and $R_3$ is methyl ($CH_3$).

4. A pharmaceutical composition comprising:
(a) a compound of formula (I)

Formula (I)

or a pharmaceutically acceptable salt thereof,
wherein $R_1$, $R_2$, and $R_3$ are, independently, hydrogen, alkoxy, hydroxyl, carboxyl, or alkyl; and,
(b) a pharmaceutically acceptable carrier.

5. A pharmaceutical composition of claim 4, wherein said compound of formula (1) is isolated and purified.

6. A method of inhibiting colorectal cancer cells comprising administering to a subject in need of such inhibition a therapeutically effective amount of a compound of claim 1.

7. A method of inhibiting colorectal cancer cells comprising administering to a subject in need of such inhibition a therapeutically effective amount of an isolated and purified compound of claim 2.

8. The method of claim 7, wherein $R_1$ and $R_2$ of the isolated and purified compound are methoxy and $R_3$ of the isolated and purified compound is methyl ($CH_3$).

9. The method of claim 8, wherein the subject is a mammal.

10. The method of claim 8, wherein the subject is a human.

11. The method of claim 6, wherein the subject is a mammal.

12. The method of claim 6, wherein the subject is a human.

* * * * *